(12) United States Patent
Cronin et al.

(10) Patent No.: US 9,084,619 B2
(45) Date of Patent: Jul. 21, 2015

(54) MICROWAVE APPLICATOR

(75) Inventors: Nigel Cronin, Bath and North East Somerset (GB); Peter Clegg, Bath and North East Somerset (GB)

(73) Assignee: AngioDynamics, Inc., Latham, NY (US)

( * ) Notice: Subject to any disclaimer, the term of this patent is extended or adjusted under 35 U.S.C. 154(b) by 1123 days.

(21) Appl. No.: 12/866,288

(22) PCT Filed: Feb. 5, 2009

(86) PCT No.: PCT/GB2009/050113
§ 371 (c)(1),
(2), (4) Date: Aug. 5, 2010

(87) PCT Pub. No.: WO2009/098513
PCT Pub. Date: Aug. 13, 2009

(65) Prior Publication Data
US 2011/0015626 A1 Jan. 20, 2011

(51) Int. Cl.
*A61F 7/12* (2006.01)
*A61B 18/18* (2006.01)
*A61B 18/00* (2006.01)

(52) U.S. Cl.
CPC .............. *A61B 18/18* (2013.01); *A61B 18/1815* (2013.01); *A61B 2018/00023* (2013.01); *A61B 2018/00166* (2013.01)

(58) Field of Classification Search
CPC ............... A61B 18/1815; A61B 18/18; A61B 2018/00023
USPC .......................................... 607/104–112, 114
See application file for complete search history.

(56) References Cited

U.S. PATENT DOCUMENTS

| 4,375,220 A | 3/1983 | Matvias |
| 7,270,656 B2* | 9/2007 | Gowda et al. .................. 606/15 |
| 2003/0060813 A1* | 3/2003 | Loeb et al. ..................... 606/17 |
| 2003/0199860 A1 | 10/2003 | Loeb et al. |
| 2004/0133254 A1 | 7/2004 | Sterzer et al. |
| 2005/0245920 A1 | 11/2005 | Vitullo et al. |

FOREIGN PATENT DOCUMENTS

| DE | 2407559 A1 | 8/1975 |
| EP | 0558297 A | 9/1993 |
| EP | 2303172 A1 | 4/2011 |
| GB | 2415630 A1 | 1/2006 |
| GB | 2457299 A | 12/2009 |
| WO | 02061880 A | 8/2002 |
| WO | 2005011049 A2 | 2/2005 |
| WO | 2007112081 A | 10/2007 |
| WO | 2009098513 A1 | 8/2009 |

* cited by examiner

*Primary Examiner* — Aaron Roane
(74) *Attorney, Agent, or Firm* — Peter J. Flora

(57) ABSTRACT

A microwave applicator having a probe which comprises an elongate shaft (14), the shaft having an external tubular wall (18), a radiating portion (15) disposed at the distal end of the shaft (14), a transmission line (17) extending to the radiating portion internally of the tubular external wall (18), and an elongate flow dividing member (19) which co-extends with the transmission line (17) longitudinally of the shaft (14), the side wall of the transmission line (17) and the side wall of the flow dividing member (19) contacting each other and contacting the internal surface of the external tubular wall (18) at two-spatially separated discrete positions, thereby defining a pair of flow channels (20, 21) inside the shaft (14). In use, cooling fluid can pass down one channel (20) and return via the other channel (21). The structure of the probe is uncomplicated and the probe is straightforward to assemble.

21 Claims, 5 Drawing Sheets

MICROWAVE APPLICATOR

This invention relates to a microwave applicator for medical use.

It's well known to ablate body tissue using a microwave applicator which heats and destroys the surrounding tissue. One use of such an applicator is in the non-invasive treatment of cancer in an internal body organ such as the liver. GB2415630 discloses an applicator of the above-mentioned type comprising a probe having a thin elongate shaft, which can be inserted into the patient. The proximal end of the probe comprises a handle which is connected to an external microwave generator by an elongate flexible cable. A thin elongate microwave transmission line extends inside the probe from the handle to a radiating tip disposed at or adjacent the distal end of the probe. In use, the microwave field radiated from the tip heats and ablates the surrounding tissue in a localised area.

A disadvantage of the above-mentioned applicator is that the probe can heat up for a variety of reasons. Firstly, power losses can occur in the transmission line extending along the probe to the tip, which power losses heat the transmission line and the surrounding parts of the probe. Secondly, the radiated microwave energy can heat the probe. Thirdly, the heat from the ablation can be conducted back along the probe. Such heating of the probe is undesirable, since it can burn the patient's skin at the point of entry of the probe or it can burn other parts of the patient's body adjacent the shaft of the probe. Indeed, UK government regulations specify that no external part of any medical apparatus should exceed 48° in temperature.

In order to overcome the above-mentioned problems, it is well known to pass a liquid, such as a saline solution, along the probe so as to cool the probe. In use, the liquid passes out of the apertures in the distal end of the probe into the surrounding body cavity. A disadvantage of this arrangement is that the liquid fills the wound and undesirably either flows out of or into the body. Furthermore, the radiated microwave energy can heat the liquid in the body cavity.

In order to overcome the above-mentioned problems, WO2005/011049, DE2407559 and U.S. Pat. No. 4,375,220 each disclose microwave applicators in which cooling fluid is passed along the probe to its distal end along one flow passage and then returned along another flow passage.

In order to achieve this, each of the above-mentioned applicators comprise a complicated arrangement of cooling pipes or formers inside the probe, which define the flow and return passages. It will be appreciated that microwave applicator probes are advantageously thin, in order to enable them to be used as non-invasively as possible. However, a disadvantage of the pipes and formers used in the above-mentioned applicators is that the flow and return passages need to be relatively large in order to achieve the desired flow rates and it will be appreciated that this correspondingly increases the overall diameter of the probe. Furthermore, the probe also needs to be of a relatively large diameter in order to facilitate the insertion of the pipes or former.

We have now devised a microwave applicator which alleviates the above-mentioned problems.

In accordance with the present invention, there is provided a microwave applicator having a probe which comprises an elongate shaft, the shaft having an external tubular wall, a microwave radiating portion disposed at the distal end of the shaft and a transmission line extending to said radiating portion internally of said tubular external wall, wherein an elongate flow dividing means extends internally along said tubular external wall and sealingly contacts the internal surface of said tubular wall along its length at two-spatially separated discrete positions around its periphery, the periphery of said flow dividing means being out of contact with said tubular wall between said two positions to define first and second discrete flow passages which extend longitudinally of said shaft for carrying cooling fluid.

In use, cooling fluid can be passed along the first passage to cool the probe, the cooling fluid then returning along the second passage. Since the flow dividing means and external tubular wall together define the flow passages, the need for complicated pipes and formers is avoided and hence the diameter of the probe can be minimised. The flow dividing means is also relatively straightforward to insert into the probe, as will be explained hereinafter.

In one embodiment, the flow dividing means comprises a single flow dividing member having an external cross-sectional shape which is different from the internal cross-sectional shape of the external tubular wall. For instance, the external cross-sectional shape of the flow dividing means may be circular and the internal cross-sectional shape of the tubular wall may be oval or vice-versa.

Said flow dividing member may comprise a hollow tube carrying said transmission line or the transmission line may itself form said flow dividing member.

In an alternative embodiment, said flow dividing means comprises said transmission line and an elongate flow dividing member which co-extends with said transmission line longitudinally of said shaft, the side wall of the transmission line and the side wall of the flow dividing member contacting each other and contacting said internal surface of the external tubular wall at said two-spatially separated discrete positions.

Said flow dividing member can be relatively thin and preferably has a diameter substantially equal to or greater than the difference between the internal diameter of said tubular external wall of the shaft and the external diameter of said transmission line.

It is often desirable to be able to sense a parameter such as temperature at the radiating tip. In order to achieve this, said flow dividing member may comprise a tube or a cable carrying one or more wires to the distal end of the shaft. In use the wire(s) may carry a measuring signal from a sensor at the distal end of the shaft.

The transmission line preferably comprises a conductor which is also connected to the sensor and forms a signal pair with the wire of the flow dividing member.

Preferably, said flow dividing member comprises a tube or a cable carrying at least one wire of a thermocouple, said one wire preferably being formed of a first metal such as constantan. The distal end of the wire of said first metal is preferably connected at its distal end to said conductor of the transmission line, the conductor being formed of a second metal such as copper. Preferably, a body of said second metal is deposited on the distal end of the wire of said first metal in order to form a reliable junction between said metals. The body of second metal is preferably held in electrical contact with said conductor of the transmission line within the probe.

Said flow passages preferably have substantially equal cross-sectional areas, the combined cross-sectional areas of the flow passages preferably being equal to the internal cross-sectional area of the tubular external wall minus the cross-sectional area of the transmission line minus the cross-sectional area of the flow dividing member.

Preferably the distal end of the flow dividing means terminates prior to said radiating portion of the probe, in order to form a cross-over between said flow passages.

Preferably at least one of said flow passages is closed at the proximal end of the probe by a seal or other member.

Preferably the proximal end of the shaft extends into a manifold, which preferably forms a handle of the probe.

Preferably the manifold comprises first and second compartments which are sealingly separated from each other, said first and second flow passages respectively communicating with said first and second compartments. Preferably the first and second compartments of the manifold are arranged at respective positions longitudinally of the axis of the shaft.

Preferably an aperture is formed in the tubular external wall of the shaft at the proximal end thereof, wherein said aperture connects a said flow passage with a said compartment of the manifold.

Preferably one of the chambers of the manifold comprises a port for connecting to an external flow duct carrying cooling fluid. This flow duct preferably carries cooling fluid into the probe from a pump or other pressurised source of cooling fluid.

Preferably the other chamber of the manifold comprises a port which connects to the distal end of an elongate flexible cable of the applicator, which cable extends from a source of microwave radiation, said cable comprising a flow duct for carrying said cooling fluid. The flow duct of the cable preferably carries cooling fluid out of the probe to a drain or a collection vessel. The flow of fluid along the cable thus further serves to cool the cable, which can become hot due to power losses.

Preferably the proximal end of the cable comprises a port which acts as an inlet or outlet of the flow duct of the cable.

Also in accordance with the present invention, there is provided a method of forming a microwave applicator probe comprising providing an elongate tube, deforming the tube perpendicular to its longitudinal axis, inserting elongate flow dividing means into the deformed tube and releasing the tube to allow the tube to recover its shape.

The deformation of the tube allows the elongate fluid dividing means to be easily inserted into the tube. Once released, the tube recovers its shape and compresses the elongate flow dividing means into a position where it contacts the internal surface of the wall at two spatially separated positions around the periphery thereof. In this manner, two sealingly-separated flow passages are formed along the tube.

Preferably the method comprises inserting an elongate transmission line into the tube. The elongate transmission line may form said flow dividing means either alone or in conjunction with an elongate flow-dividing member. In the latter case, the transmission line and the flow dividing member may be inserted into the tube simultaneously or one after the other. In the latter case, one of the members may be inserted into the tube prior to the deformation thereof.

Embodiments of the present invention will now be described by way of examples only and with reference to the accompanying drawings, in which.

Figure 1:
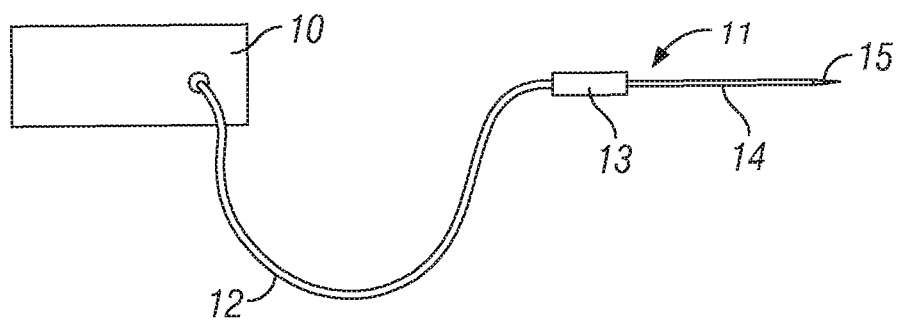
FIG. 1 is a schematic view of a first embodiment of microwave applicator in accordance with the present invention.

Referring to FIG. 1 of the drawings, there is shown a microwave applicator probe comprising a microwave generator 10 connected to an applicator probe 11 via an elongate flexible feed cable 12. The probe 11 comprises a handle portion 13 and an elongate shaft portion 14 extending from the handle 13. In use, the generator 10 generates a microwave signal which is transmitted along the feed cable 12 to the probe 11. The microwave signal is then transmitted along the shaft 14 of the probe to a radiating tip 15 at the distal end thereof.

Figure 2:
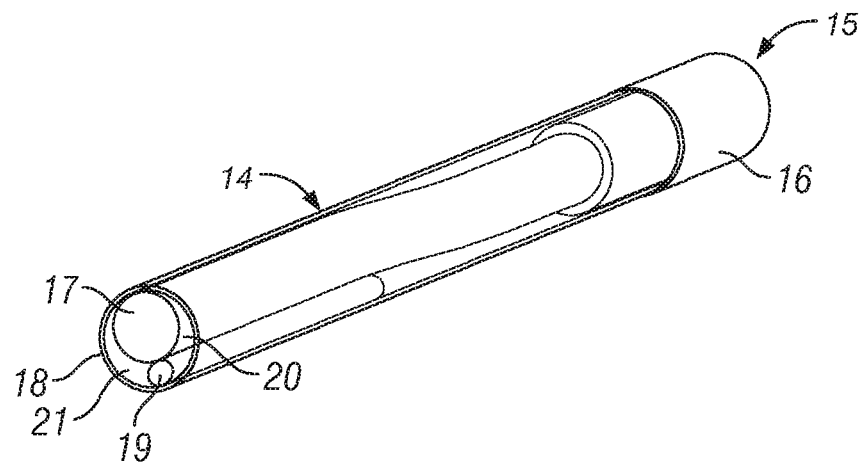
FIG. 2 is a perspective outline view of the distal end of a probe of the applicator of FIG. 1.

Referring to FIG. 2 of the drawings, the shaft 14 comprises an external elongate tubular wall 14 formed of stainless steel. A co-axial transmission line 17 extends internally of the tubular wall 14, the transmission line 17 being coupled at its proximal end to the microwave feed cable 12 and at its distal end to a radiating antenna 16 disposed inside the tip 15 of the probe 11. An elongate flow dividing member 19, in the form of a solid cable or wire, co-extends with the co-axial transmission line 17 along a substantial part of the length thereof, the member 19 terminating a short distance away from the radiating antenna 16.

The combined diameter of the transmission line 17 and the flow dividing member 19 is slightly greater than the internal diameter of the tubular external wall 18, such that the transmission line 17 and flow dividing member both positively contact the internal surface of the external tubular wall 18 and each other along a substantial part of the length of the shaft 14. The transmission line 17 and flow dividing member 19 thus together define two flow channels 20, 21, which extend longitudinally of the shaft 14 from the proximal end to the point at which the flow dividing member 19 terminates. The two flow channels 20, 21 are interconnected beyond the point at which the flow dividing member 19 terminates.

Figure 3:
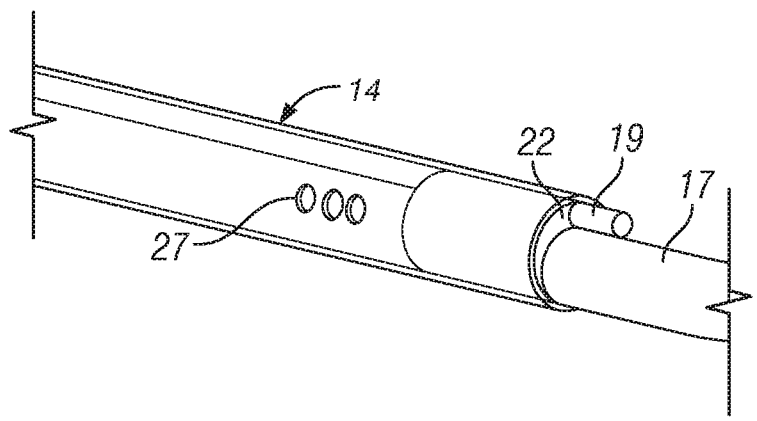
FIG. 3 is a perspective outline view of the proximal end of a shaft of the probe of the applicator of FIG. 1.
Figure 4:
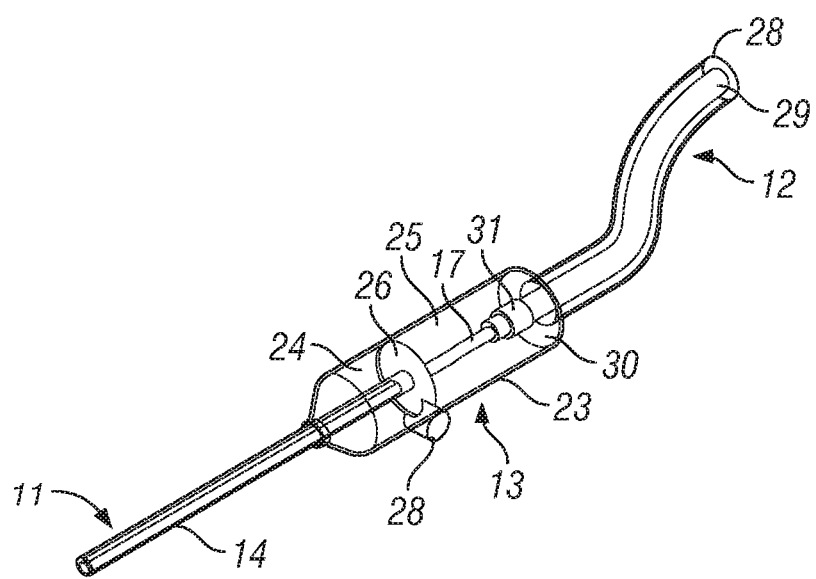
FIG. 4 is a perspective outline view of the proximal end of the probe and a microwave feed cable of the applicator of FIG. 1.
Figure 5:
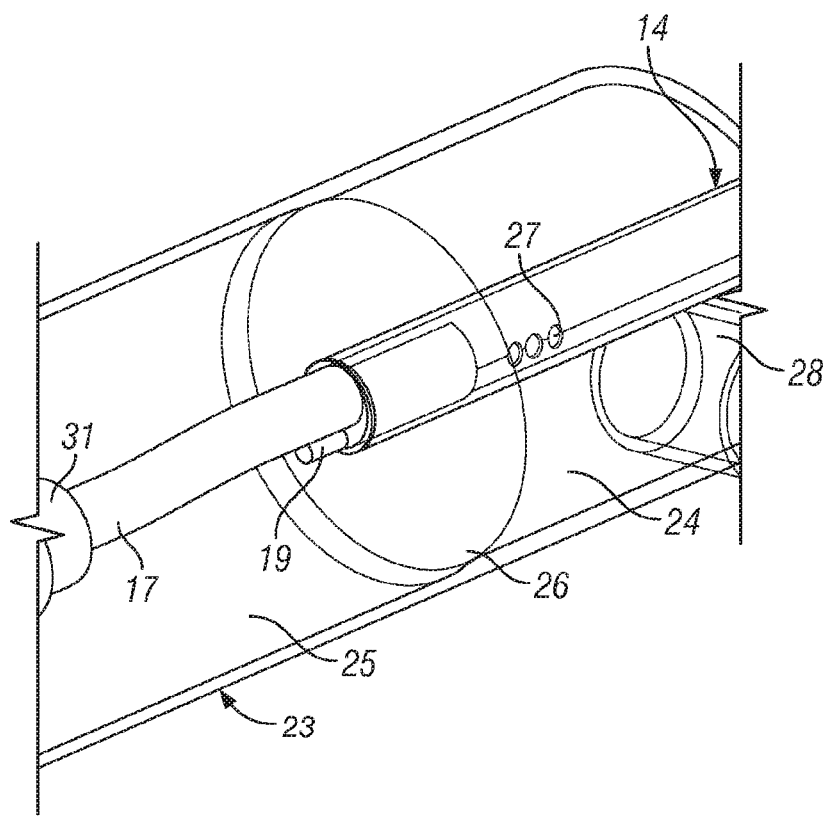
FIG. 5 is a perspective outline view of a portion of a manifold of the probe of the apparatus of FIG. 1.

Referring to FIGS. 3 and 4 of the drawings, one of the channels 20 is sealed by a member 22 at the proximal end of the shaft 14. A plurality of apertures 27 are formed in the external tubular wall 18 of the shaft 14 at the proximal end thereof, the apertures 27 communicating with the sealed channel 20. The proximal end of the shaft 14 extends into a manifold 23 disposed inside the handle 13 of the probe 11. The manifold 23 is generally cylindrical and is divided into two axially-disposed chambers 24, 25 by a boundary wall 26 which extends normal to the longitudinal axis of the shaft 14. The proximal end of the shaft 14 extends into the manifold 23 and through the boundary wall 26, such that the apertures 27 open into the distal chamber 24 of the manifold 23, the second (un-sealed) flow channel 21 of the shaft 14 opening into the proximal chamber 25 of the manifold 23. An inlet port 28 extends radially outwardly from the side wall of the manifold 23, the inlet port 28 communicating with the distal chamber 24 of the manifold 23.

The proximal end wall 13 of the manifold 23 is connected to the feed cable 12, the feed cable 12 comprising an outer tube 28 and a co-axial cable 29 extending loosely inside the tube 28. The co-axial cable 29 extends through the proximal end wall 30 of the manifold 23 and is connected inside the chamber 25 to the co-axial transmission line 17 by a co-axial coupling 31. The distal end of the tube 28 is sealingly coupled to an aperture in the proximal end wall 30 of the manifold 23, such that the interior of the tube 28 opens into the proximal chamber 25 of the manifold 23.

Figure 6:
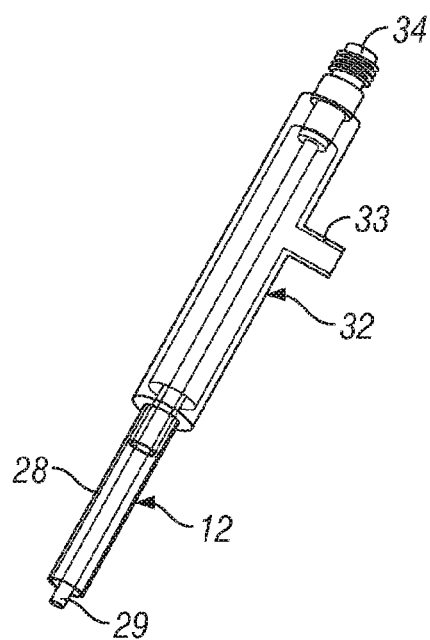
FIG. 6 is a perspective outline view of an outlet chamber of the feed cable of the applicator of FIG. 1.

Referring to FIG. 6 of the drawings, the proximal end of the feed cable 12 is connected to an elongate cylindrical outlet chamber 32. The proximal end of the tube 28 of the feed cable 12 is coupled to the outlet chamber 32, such that the interior of the tube 28 opens into the outlet chamber 32. The co-axial cable 29 extends through the outlet chamber 32 to a co-axial connector 34 on the external face of the proximal end wall of the chamber 32. An outlet port 32 extends radially outwardly from the side wall of the outlet chamber 32.

In use, the co-axial connector 34 is connected to the microwave generator 10. The inlet port 28 of the manifold 23 is connected to a pump via an elongate tube (not shown). The outlet port 33 is connected to a collection vessel via an elongate tube (not shown). When energised, the pump pumps cooling fluid into the distal chamber 24 of the manifold 23 through the inlet port 28. The cooling fluid then flows through the apertures 27 in the external tubular wall 18 of the shaft 14 and into the flow channel 20. The cooling fluid then flows longitudinally of the shaft 14, thereby cooling the external wall 18 of the shaft and the transmission line 17. The cooling fluid then crosses from the flow channel 20 to the other flow channel 21 at the distal end of the shaft 14, beyond the point at which the flow dividing member 19 terminates. The cooling fluid then returns along the shaft 14 via the cooling channel 21, whereupon it flows into the proximal chamber 25 of the manifold 23. The fluid then flows out of the manifold 23 and into the feed cable 12, whereupon it flows along the cable 12 in an annular flow channel defined between the outer tube 28 and the co-axial cable 29. The fluid then flows out of the outlet chamber 32 through the outlet port 33 to a collection vessel. In this manner, the cooling fluid also cools the co-axial cable 29.

Figure 7:
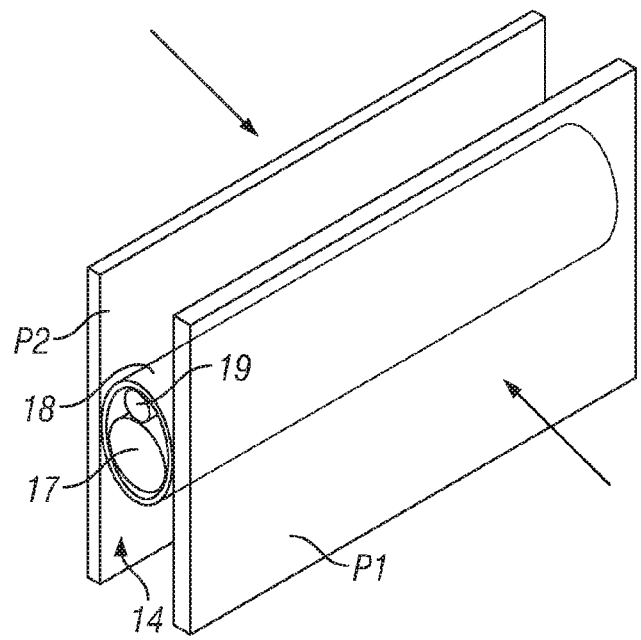
FIG. 7 is a perspective schematic view illustrating the method of manufacture of the shaft of the probe of the applicator of FIG. 1.

Referring to FIG. 7 of the drawings, the co-axial transmission line 17 and the flow dividing member 19 are inserted into the external tubular wall 18 of the shaft 14 by compressing the external tubular wall 18 transverse its longitudinal axis into an oval shape. The transmission line 17 and the flow dividing member 19 can then be easily inserted into the deformed external tubular wall 18. Once inserted, the applied force can be removed, thereby allowing the external tubular wall 18 to recover its shape, such that the co-axial transmission line 17 and the flow dividing member 19 become compressed against each other and against the external tubular wall 18.

Figure 8:
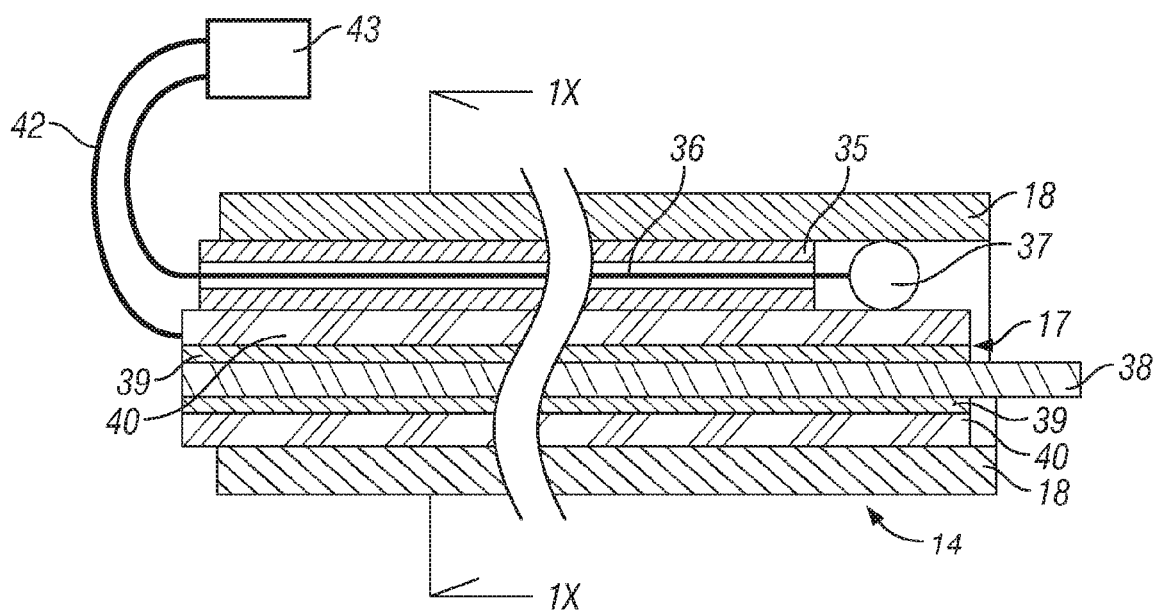
FIG. 8 is a longitudinal sectional view through the shaft of a probe of a second embodiment of microwave applicator probe in accordance with the present invention.
Figure 9:
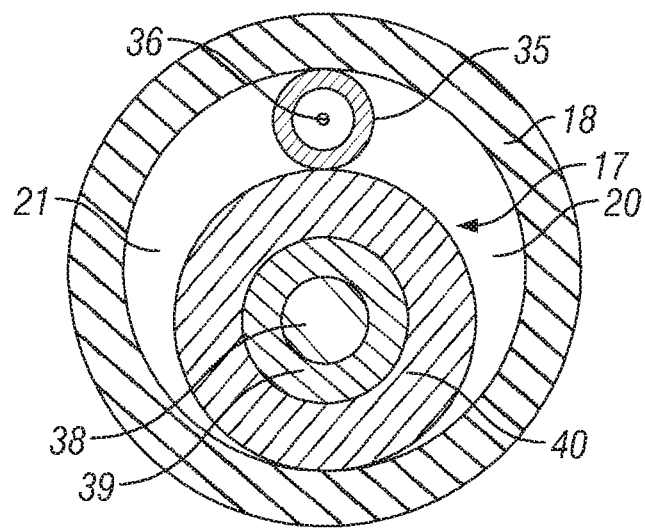
FIG. 9 is a sectional view along the line IX-IX of FIG. 8.

Referring to FIGS. 8 and 9 of the drawings, there is shown an alternative embodiment of microwave applicator probe which is similar to the probe of FIGS. 1-7 and like parts are have given like reference numerals. In this embodiment, the elongate flow dividing member 19 is replaced by a thin tube, e.g formed of stainless steel. An elongate insulated wire 36 of constantan extends from a measuring instrument 43 through the tube 35. The insulation is removed from the distal end of the constantan wire and a body 37 of copper material is deposited onto the exposed conductor of the constantan wire 36. The transmission line 17 comprises an outer copper sleeve 40. An elongate central conductor 38 extends inside the copper sleeve 40 and is insulated therefrom by a dielectric sleeve 39. The body 37 of copper on the constantan wire 36 makes contact with the copper sleeve 40 of the transmission line 17. The body 37 of copper has a diameter which is substantially equal to the diameter of the tube 35, such that it is held tightly in contact with the copper sleeve 40 of the transmission line 17. The external surface of the copper body 37 may be electro-plated to ensure a reliable contact with the copper sleeve 40 of the transmission line 17. The proximal end of the copper conductor 40 is connected via a wire 42 to the measuring instrument 43. The tube 35 is preferably sealed by the constantan wire 36 or another member against fluid flow. In this way, the risk of fluid using the tube 35 as a return path is avoided.

It will be appreciated that a complete circuit from the thermocouple instrument 43 is thus created by the constantan wire 36, the copper body 37 and the copper sleeve 40 of the transmission line 17. The copper-constantan junction inside the body 37 forms a thermocouple junction which can be used to provide an indication of the temperature at the tip of the probe 11.

The two thermocouple wires 36,42 extending from the measuring instrument 43 preferably extend into the outlet manifold 32 and along the cable 12 in the annular flow channel defined between the outer tube 28 and the co-axial cable 29. The wires 36,42 then extend through the manifold 13 to the shaft 14 of the probe 11. This arrangement helps to hide the wires 36,42 and improves the overall appearance of the applicator.

Figure 10:
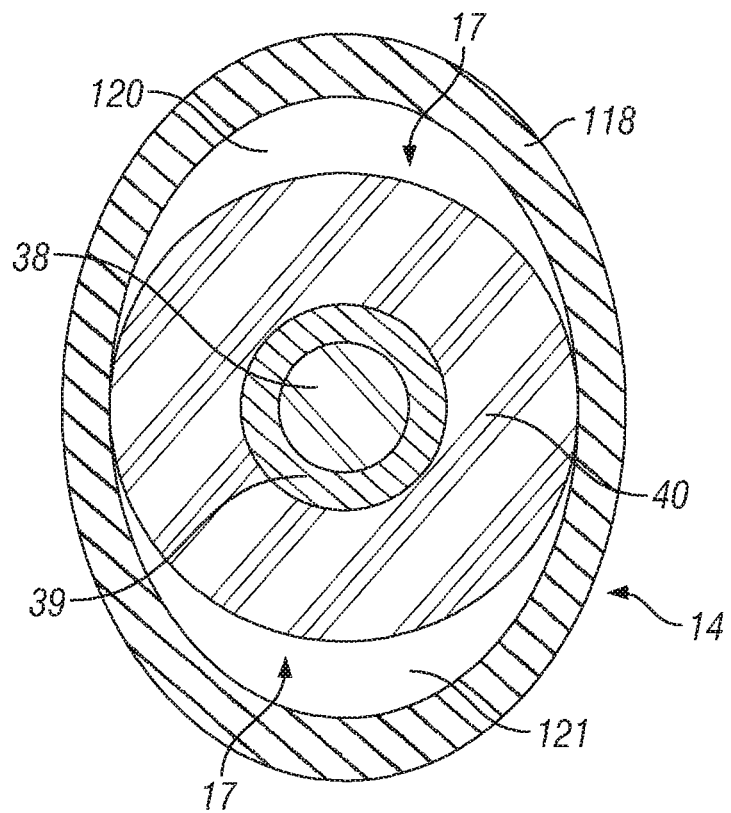
FIG. 10 is a transverse sectional view through the shaft of a probe of a third embodiment of microwave applicator probe in accordance with the present invention.

Referring to FIG. 10 of the drawings, there is shown an alternative embodiment of microwave applicator probe, which is similar to the embodiment of FIGS. 8 and 9 and like parts are given like reference numerals. In this embodiment, the separate flow-dividing member 19 is omitted and instead, the transmission line 17 acts on its own to define two flow-channels 120, 121. This is achieved by providing the shaft 14 with an external tubular wall 118 which is normally oval in section. The transmission line 17 is inserted into the external wall 118 by deforming the wall transverse its longitudinal axis until it comes generally circular in shape: this allows the transmission line 17 to be inserted, whereupon the deforming force can be removed such that the transmission line 17 contacts the external wall 118 at diametrically opposed positions.

A microwave applicator probe in accordance with the present invention is relatively simple and inexpensive in construction, yet enables the probe to be reliably cooled.

The invention claimed is:

1. A microwave applicator comprising:
    an elongated shaft having an external tubular wall;
    a microwave radiating portion near a distal end of the shaft;
    a flow dividing element comprising of a transmission line and a flow dividing member, the transmission line extending to the microwave radiating portion, the transmission line and flow dividing member extend longitudinally along the shaft, a first side of the transmission line outer wall and a first side of the flow dividing member outer wall contacting each other, a second side of the transmission line outer wall and a second side of the flow dividing member outer wall contacting the internal surface of the external tubular wall at two-spatially separated locations to define a first flow passage and a second flow passage which extend longitudinally along the shaft.

2. A microwave applicator as claimed in claim 1, in which the external cross-sectional shape of the flow dividing member is circular and the internal cross-sectional shape of the tubular wall is oval or vice-versa.

3. A microwave applicator as claimed in claim 1, in which said flow dividing member comprises a hollow tube.

4. A microwave applicator as claimed in claim 1, in which said flow dividing member is formed by a solid cable or wire.

5. A microwave applicator as claimed in claim 1, in which said flow dividing member has a diameter equal to or greater than the difference between the internal diameter of said tubular external wall of the shaft and the external diameter of said transmission line.

6. A microwave applicator as claimed in claim 1, in which said flow passages have substantially equal cross-sectional areas, the combined cross-sectional areas of the flow passages being equal to the internal cross-sectional area of the tubular external wall minus the cross-sectional area of the transmission line minus the cross-sectional area of the flow dividing member.

7. A microwave applicator as claimed in claim 1, in which the distal end of the flow dividing element terminates prior to said radiating portion of the applicator, in order to form a cross-over between said flow passages.

8. A microwave applicator as claimed in claim 1, in which at least one of said flow passages is closed at the proximal end of the applicator by a seal.

9. A microwave applicator as claimed in claim 1, in which the proximal end of the shall extends into a manifold.

10. A microwave applicator as claimed in claim 9, comprising a handle at the proximal end of the shaft which comprises said manifold.

11. A microwave applicator as claimed in claim 9, in which the manifold comprises first and second compartments which are sealingly separated from each other, said first and second flow passages respectively communicating with said first and second compartments.

12. A microwave applicator as claimed in claim 11, in which the first and second compartments of the manifold are arranged at respective positions longitudinally of the axis of the shaft.

13. A microwave applicator as claimed in claim 11, in which an aperture is formed in the tubular external wall of the shaft at the proximal end thereof, wherein said aperture connects a said flow passage with a said compartment of the manifold.

14. A microwave applicator as claimed in claim 11, in which one of the chambers of the manifold comprises a port for connecting to an external flow duct carrying cooling fluid.

15. A microwave applicator as claimed in claim 14, in which said flow duct carries cooling fluid into the applicator from a pump or other pressurized source of coo ling fluid.

16. A microwave applicator as claimed in claim 14, in which the other chamber of the manifold comprises a port which connects to the distal end of an elongate flexible cable of the applicator, which cable extends from a source of microwave radiation, said cable comprising a flow duct for carrying said cooling fluid.

17. A microwave applicator as claimed in claim 16, in which the flow duct of the cable carries cooling fluid out of the applicator to a drain or a collection vessel.

18. A microwave applicator as claimed in claim 16, in which the proximal end of the cable comprises a port which acts as an inlet or outlet of the flow duct oft cable.

19. A microwave applicator as claimed in claim 16, in which the proximal end of the shaft comprises a fluid inlet and a fluid outlet respectively connected to said first and second passages.

20. A microwave applicator as claimed in claim 1, comprising means for creating a fluid flow through the applicator such that fluid flows along said first passage towards the distal end of the shaft and returns along said second passage.

21. The microwave applicator as claimed in claim 1, wherein the flow dividing member having an outer diameter, the transmission line having an outer diameter, the external tubular wall having an inner diameter, the combination of the flow dividing member outer diameter and transmission line outer diameter creates an interference fit with the internal diameter of the external tubular wall.

* * * * *